United States Patent [19]

Weeks

[11] Plant 4,796

[45] Jan. 19, 1982

[54] ROSE PLANT

[76] Inventor: O. L. Weeks, 4759 Philadelphia St., Chino, Calif. 91710

[21] Appl. No.: 177,261

[22] Filed: Aug. 11, 1980

[51] Int. Cl.[3] ..... A01H 5/00

[52] U.S. Cl. ..... Plt./2

[58] Field of Search ..... Plt./2

*Primary Examiner*—Robert E. Bagwill
*Attorney, Agent, or Firm*—Vincent G. Gioia

[57] ABSTRACT

A new climbing sport of the rose variety described in U.S. Plant Pat. No. 4,552.

1 Drawing Figure

1

The present invention relates to a new and distinct climbing sport of the bush variety described in U.S. Plant Pat. No. 4,552 which was discovered by me on my property.

This sport was discovered on a routine inspection of bush "Paradise" plants and I noticed that one plant had produced a climbing cane. I thereupon took steps to preserve the sport. Asexual reproduction by budding of the new variety as performed in San Bernardino County, Calif., shows that the foregoing distinguishing characteristics come true to form and are established and transmitted through succeeding propagations. Continued observations of the asexual reproductions conclusively established that the new sport was substantially identical with the parent variety "Paradise" (described in U.S. Plant Pat. No. 4,552) except for the climbing habit aforementioned and for the fact that the flowers are produced on stems that grow as laterals from the climbing canes. All of these distinguishing features and characteristics of the new sport are fixed and transmissable by asexual reproduction and as far as I know, the bush plant of "Paradise" has never previously exhibited a climbing habit of growth and I am

2 convinced that this sport is definitely a new and distinct variety.

The new and improved rose variety which I have discovered is substantially identical with the bush variety in all respects except for the climbing habit of growth. The new variety produces canes of eight feet in length or more in contrast to normal healthy growth of the bush variety which attains a height of four to five feet under similar growing conditions. All other botanical features substantially conform to the bush variety and are fully set forth in U.S. Plant Pat. No. 4,552.

The accompanying drawing shows typical specimens of the vegetative growth and climbing habit of the new variety as nearly true as it is reasonably possible to make in an illustration of this character.

I claim:

1. A new and distinct climbing variety of rose plant substantially as shown and described, which is a sport of the bush variety described in U.S. Plant Pat. No. 4,552, characterized particularly by its climbing habit of growth producing long canes and the habit of bearing flowers on stems which grow as laterals from the climbing canes.

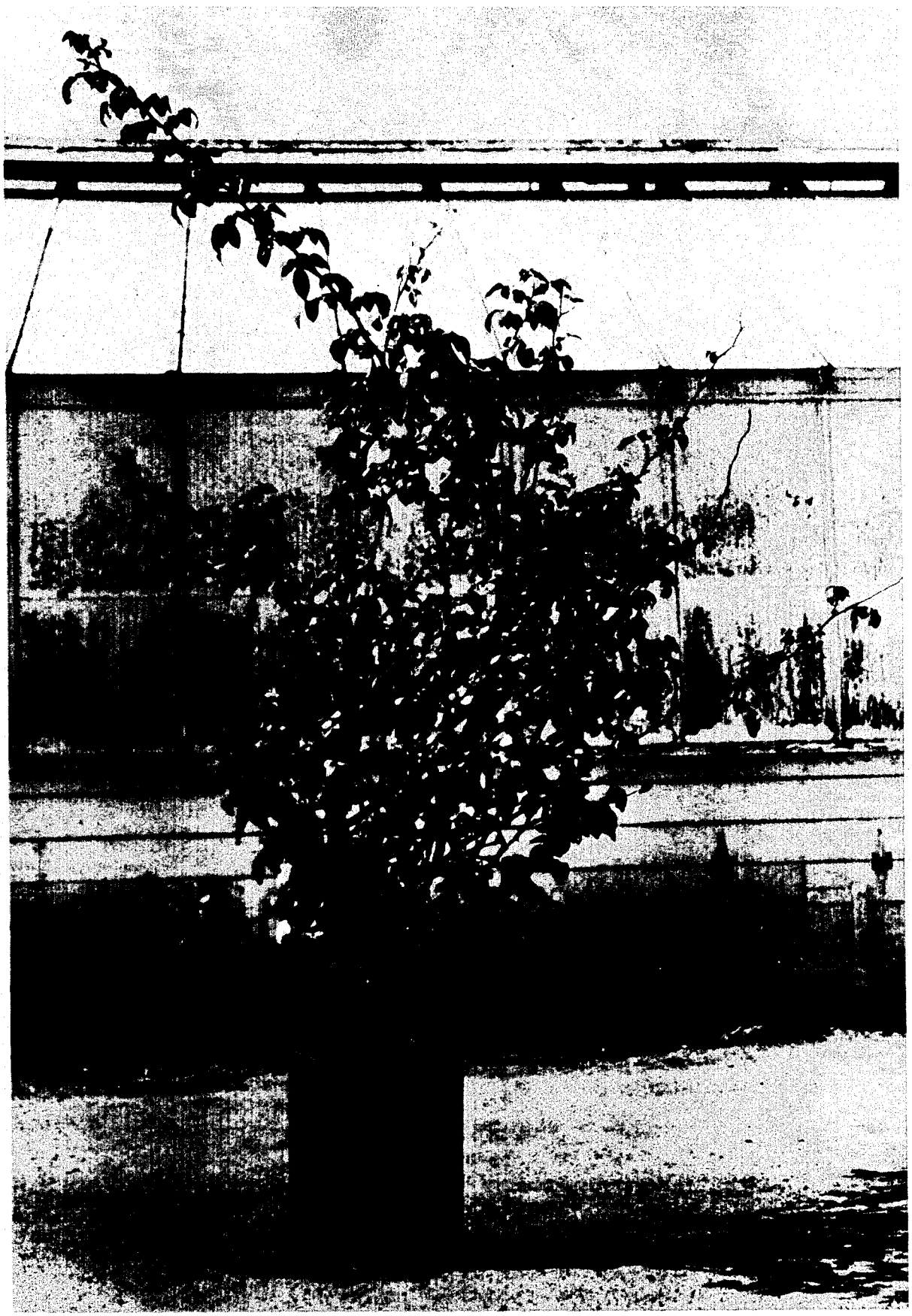

* * * * *